(12) United States Patent
Wilhelm et al.

(10) Patent No.: US 6,774,267 B2
(45) Date of Patent: Aug. 10, 2004

(54) PHENOLIC COMPOUNDS DERIVED FROM DIALKOXYETHANALS, THEIR PREPARATION PROCESS AND THEIR APPLICATION

(75) Inventors: Didier Wilhelm, Issy les Moulineaux (FR); Florence Esmard, Compiegne (FR)

(73) Assignee: Clariant France, Puteaux (FR)

( * ) Notice: Subject to any disclaimer, the term of this patent is extended or adjusted under 35 U.S.C. 154(b) by 0 days.

(21) Appl. No.: 09/778,353

(22) Filed: Feb. 7, 2001

(65) Prior Publication Data

US 2001/0016664 A1 Aug. 23, 2001

(30) Foreign Application Priority Data

Feb. 7, 2000 (FR) .......................................... 00 01483

(51) Int. Cl.[7] .............................................. C07C 43/30
(52) U.S. Cl. ........................ 568/592; 8/116.1; 8/115.56
(58) Field of Search ........................... 568/592; 8/116.1, 8/115.56

(56) References Cited

U.S. PATENT DOCUMENTS 4,900,324 A 2/1990 Chance et al.
5,254,753 A * 10/1993 Durrwachter

FOREIGN PATENT DOCUMENTS

| JP | 2002-338513 | * 11/2002 |
| WO | WO 97/11119 | 3/1997 |
| WO | WO-02/40562 | * 5/2002 |

OTHER PUBLICATIONS

Kirk–Othmer Encyclopaedia, vol. 18, 4th Edition, Wiley Interscience, p. 603–644, 1996.
EPO Search Report 2001.
Chemical Abstracts, vol. 67, No. 11, 1967, abstract No. 53832n "Problems in the synthesis of nonnitrigenous metabolites of catechol amines" & Recent Results Cancer Res., No. 2, 1966, pp. 22–26, "Problèms posés à l'Organicien par la Synthèse des Métabolites non Azotés des Catécholamines", Jean Gardent et Joseph Likforman (No Translation).

* cited by examiner

*Primary Examiner*—Michael L. Shippen
(74) *Attorney, Agent, or Firm*—Scott E. Banf; Anthony A. Bisulca

(57) ABSTRACT

New phenolic compounds of formula (I)

(I)

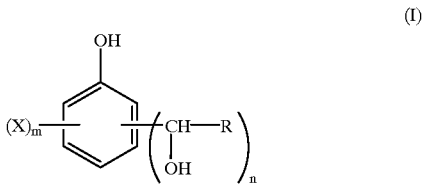

R=$C_3$–$C_{17}$ dialkoxymethyl group, 1,3-dioxolan-2-yl group optionally substituted on peaks 4 and/or 5 by one or more $C_1$–$C_8$ alkyls or 1,3-dioxan-2-yl group optionally substituted on peaks 4 and/or 5 and/or 6 by one or more $C_1$–$C_8$ alkyls.

n=1, 2 or 3, the group or groups

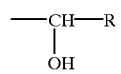

are in o and/or p position of the OH of the cycle
m=from 0 to 4-n, X=functional group such as OH or Hal or $C_1$–$C_8$ alkyl or alkoxy group or $C_5$–$C_{12}$ aryl group and optionally 1 or 2 heteroatoms such as N or O, or carboxy or —CO—Y group where Y=$C_1$–$C_8$ alkyl or alkoxy or amido or amino or thiol group, on condition that at least one of the ortho or para positions of the phenolic cycle is substituted by a hydrogen, and their salts with the alkali metals, alkaline-earth metals and amines.

15 Claims, 1 Drawing Sheet

PHENOLIC COMPOUNDS DERIVED FROM DIALKOXYETHANALS, THEIR PREPARATION PROCESS AND THEIR APPLICATION

FIELD OF THE INVENTION

The present invention relates to new phenolic compounds derived from dialkoxyethanals, their preparation process and their application.

SUMMARY OF THE INVENTION

The benefit of the new phenolic compounds derived from dialkoxyethanals is twofold. First of all, new phenolic compounds with a protected aldehyde function can be obtained, which can be used as synthesis intermediates. Then, crosslinkers of phenolic type can be prepared but with the advantage that they do not release formaldehyde during their synthesis or their use. In order to have an idea of the benefit of such crosslinkers, reference may be made to the general article on phenolic resins, advanced in the Kirk-Othmer encyclopaedia, vol. 18, 4$^{th}$ edition, Wiley Interscience, 1996, p 603–644.

DESCRIPTION OF THE PREFERRED EMBODIMENTS

A subject of the present invention is thus new phenolic compounds derived from dialkoxyethanals of formula (I)

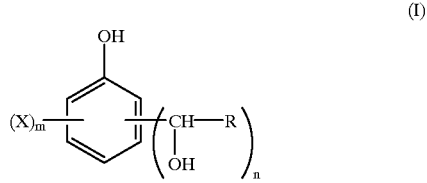

(I)

in which
  R is a dialkoxymethyl group with from 3 to 17 carbon atoms, a 1,3-dioxolan-2-yl group optionally substituted on peaks 4 and/or 5 by one or more alkyl groups comprising from 1 to 8 carbon atoms or a 1,3-dioxan-2-yl group optionally substituted on peaks 4 and/or 5 and/or 6 by one or more alkyl groups comprising from 1 to 8 carbon atoms.
  n has the value 1, 2 or 3 and the group or groups

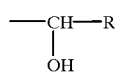

are in ortho and/or in para position of the OH group of the cycle
  m represents from 0 to 4-n and X represents a functional group such as hydroxyl or halogen such as chlorine, fluorine, bromine, iodine or an alkyl or alkoxy group comprising from 1 to 8 carbon atoms or aryl group comprising from 5 to 12 carbon atoms and optionally 1 or 2 heteroatoms such as nitrogen or oxygen or carboxy or —CO—Y group in which Y represents an alkyl or alkoxy radical containing from 1 to 8 carbon or amido or amino or thiol radical, on condition that at least one of the ortho or para positions of the phenolic cycle is substituted by a hydrogen, with the exception of the compound 1 described by J. Gardent and J. Likforman, Recent Results Cancer Res. 1966, 22, 23–26.

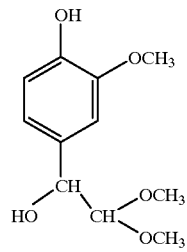

1 and their salts with the alkali metals, alkaline-earth metals and amines.

More particularly, a subject of the present invention is new phenolic compounds derived from dialkoxyethanals of formula (I) in which:

R is a dialkoxymethyl group comprising from 3 to 10, in particular 3 to 7 carbon atoms, preferably a dimethoxymethyl or diethoxyethyl group
  n has the value 2 or preferably 1, the group

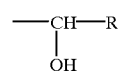

being in ortho position or in para position of the OH group of the cycle, m represents 0 or 1
  X represents a hydroxyl or halogen group such as chlorine or an alkyl group such as methyl, ethyl or tert-butyl, or alkoxy group such as methoxy or ethoxy, or carboxyl group such as methyl carboxylate or ethyl carboxylate.
  In other preferential conditions, when several groups X are present, they are identical. The alkyl groups comprising from 1 to 8 carbon atoms preferably contain from 1 to 5 carbon atoms, in particular from 1 to 3 carbon atoms.

In an even more particular manner, a subject of the present invention is new phenolic compounds derived from dialkoxyethanals of general formula (I) and more particularly the following compounds:

4-(1-hydroxy-2,2-dimethoxy-ethyl)-phenol
  2-(1-hydroxy-2,2-dimethoxy-ethyl)-phenol
  4-chloro-2-(1-hydroxy-2,2-dimethoxy-ethyl)-phenol
  2-(1-hydroxy-2,2-dimethoxy-ethyl)4-methyl-phenol
  4-tert-butyl-2-(1-hydroxy-2,2-dimethoxy-ethyl)-phenol
  3-(1-hydroxy-2,2-dimethoxy-ethyl)4-hydroxy-methyl-benzoate.

A subject of the invention is also a preparation process for phenolic compounds derived from dialkoxyethanals of formula (I) and their salts with the alkali metals, alkaline-earth metals and amines characterized by the fact that, in the presence of a base:

a phenol of formula (II)

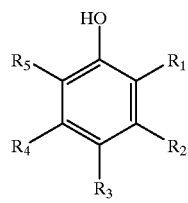
(II)

in which $R_1$, $R_2$, $R_3$, $R_4$, $R_5$ can be a hydroxyl radical, a halogen such as chlorine, fluorine, bromine, iodine or an alkyl radical comprising from 1 to 8 carbon atoms or an aryl radical or an alkoxy radical comprising from 1 to 8 carbon atoms or an ester radical comprising from 1 to 8 carbon atoms or an amide radical or an amine radical or a thiol radical, on condition that at least one of the ortho or para positions of the phenolic cycle is substituted by a hydrogen.

is reacted with an aldehyde of formula (III)

(III)

in which R is a dialkoxymethyl group, a 1,3-dioxolan-2-yl group optionally substituted on peaks 4 and/or 5 by one or more alkyl groups or a 1,3-dioxan-2-yl group optionally substituted on peaks 4 and/or 5 and/or 6 by one or more alkyl groups in order to obtain the expected compound.

In preferential conditions of implementation of the invention, the phenolic compounds derived from dialkoxyethanals are prepared as follows: 0.1 to 10 moles of aldehyde of formula (III) and 0.1 to 2 base moles are introduced into a flask per 1 mole of phenol of formula (II). The whole is reacted at a given temperature for a given time. A crude reaction mixture is obtained of which the expected product or products are isolated if desired.

In other preferential conditions of the invention, 0.1 to 5 moles of aldehyde of formula III per 1 mole of phenol of formula 11 in the presence of 0.1 to 1 mole of base.

Still in other preferential conditions of the invention, the base necessary for the catalysis of the reaction can be a tertiary amine such as tributylamine or triethylamine or an alkyl metal hydroxide such as sodium hydroxide or potassium hydroxide, or an alkali metal carbonate such as sodium carbonate or potassium carbonate.

In yet other preferential conditions of the invention, the aldehyde of formula III can be dimethoxyacetaldehyde, diethoxyacetaldehyde, dibutoxyacetaldehyde, 2-formyl-1,3-dioxolane or 5,5-dimethyl 2-formyl 1,3-dioxane.

The phenolic compounds derived from dialkoxyethanals of formula (I) and their salts with the alkali metals, alkaline-earth metals and amines, subject of the invention, can advantageously be used as synthesis intermediates in pharmacy or in plant pharmacy. They can also serve for the preparation of phenolic resins without formaldehyde, the preparation of crosslinkers without formaldehyde of various substrates such as cellulose substrates, non-woven substrates, nylon, polyester, glass.

Finally, a subject of the present invention is the use of the phenolic compounds derived from dialkoxyethanals of general formula (I) and their salts with the alkali metals, alkaline-earth metals and amines, either as synthesis intermediate, or as intermediate for the preparation of phenolic resins without formaldehyde, or as crosslinker without formaldehyde with a substrate which can be a cellulose substrate, a non-woven substrate, of nylon, polyester or glass.

EXAMPLES

The following examples will allow the invention to be better understood.

EXAMPLE 1

Figure 1:
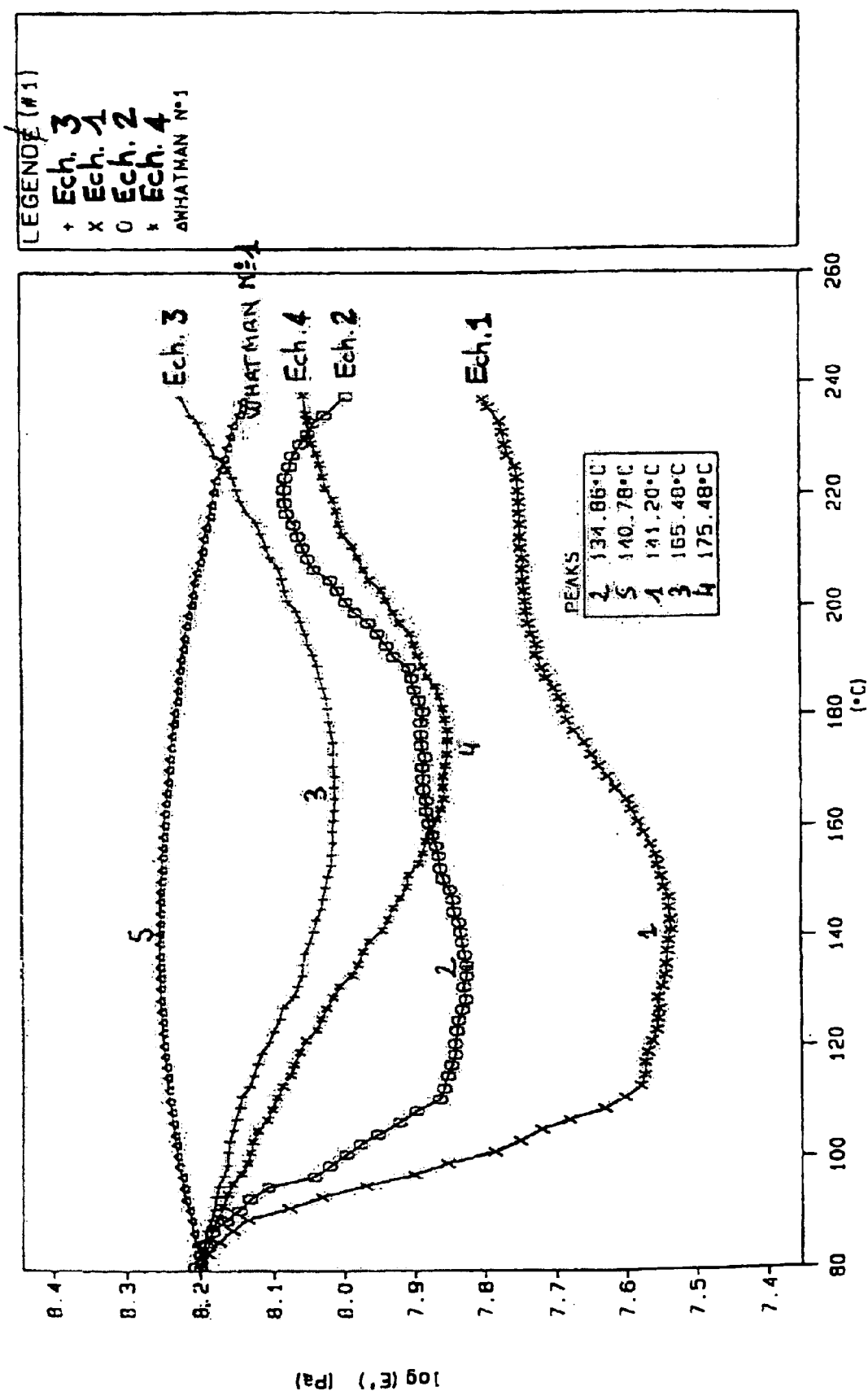
FIG. 1 represents the variation of the flexural elastic modulus in relation to temperature.

There are introduced into a 1 L flask:

475.3 g (5 moles) of 99% phenol 86.7 g (0.5 mole) of dimethoxyethanal in 60% aqueous solution 93.4 g (0.5 mole) of tributylamine.

The reaction mixture is heated to 50° C. and the course of the reaction is monitored by HPLC. After 24 hours of reaction, the mixture is cooled to ambient temperature.

655 g of a crude solution are obtained, containing the phenol in excess, the tributylamine and a mixture of 4-(1-hydroxy-2,2-dimethoxy-ethyl)-phenol 2 and 2-(1-hydroxy-2,2-dimethoxy-ethyl)-phenol 3 with a yield relative to the dimethoxyethanal of 71% for the para compound 2 and 27% for the ortho compound 3, i.e. a total yield of 98%.

A purification of the reaction mixture can be carried out neutralizing the latter with 990 g of a 20% aqueous soda solution (5 moles of soda). 2 phases are then obtained which are separated.

The organic upper phase (90 g) is more than 98% composed of tributylamine. The aqueous lower phase (1547 g) is reacidified by 860 g of a 20% aqueous HCI solution to pH 5–6.

The medium then decants of itself. This acidified aqueous phase is then extracted with 2 times 500 ml of methyl tert-butyl ether (MTBE). The organic phases obtained are then combined and concentrated under vacuum to give 445 g of a mixture of expected products 2 and 3 and phenol. The phenol is eliminated by distillation under forced vacuum (5 mm Hg at 50° C.). The residual mixture, containing less than 5% phenol, is then recrystallized from an isopropyl ether/isopropanol mixture.

The precipitate then obtained is filtered, washed with isopropyl ether and dried to give 10.7 g (yield 10.2%) of the expected para compound 2.

A second jet on the mother liquors leads in the same conditions to an extra 15.6 g (yield 15.8%) of the para compound 2.

The 1H NMR, 13C RMN and mass spectrography analyses are in agreement with the expected para compound 2.

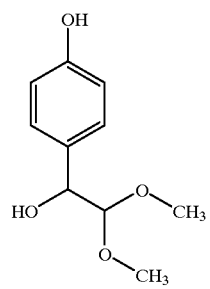

2

Description of the Proton Spectrum of 2
3.12 ppm (s; 3H; O—CH3)
3.30 ppm (s; 3H; OCH3)
4.19 ppm (d; J=6.6 Hz; 1H; CH—(OCH3)$_2$)
4.33 ppm (dd; J=4.3 Hz & J=6.3 Hz; 1H; CH—OH)
5.15 ppm (d; J=4.7 Hz; 1H; CH—OH)
6.87 ppm (AB system; JAB=8.6 Hz; 4H; 4Hφ)
9.31 ppm (s; 1H; φ-OH)
Description of the Carbon 13 Spectrum of 2
53.9 ppm; (1 CH3; OCH3)
54.9 ppm; (1 CH3; OCH3)
72.6 ppm; (1 CH; CH—OH)
107.4 ppm; (1 CH; CH—(OCH3)$_2$)
114.5 ppm; (2 CH; 2CHφ in ortho of the Cq-OH)
128.5 ppm; (2 CH; 2CHφ in meta of the Cq-OH)
132.2 ppm; (1 Cq; Cqφ—CH)
156.4 ppm; (Cq; Cqφ-OH)

The melting point of this para compound 2 is 90.4° C.

The remaining mother liquors (198 g) consist of a mixture enriched in ortho compound 3. This mixture contains 29.2% of para compound 2 and 14.5% of ortho compound 3. The analysis of this mixture by 1H NMR is in conformity with the presence of the ortho compound 3.

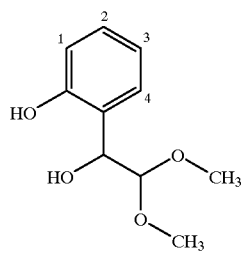

3

Description of the Proton Spectrum of 3
3.17 ppm (s; 3H; OCH3)
3.30 ppm (s; 3H; OCH3)
4.39 ppm (d; J=5.9 Hz; 1H; CH—(OCH3)$_2$)
4.86 ppm (dd; J=5.5 Hz & J=5.5 Hz; 1 H; CH—OH)
5.16 ppm (d; J=5.5 Hz; 1H; CH—OH)
6.76 ppm (multiplet; 2H; H1 and H3)
7.02 ppm (m; J=7.0 Hz & J=2.0 Hz; H2)
7.25 ppm (dd; J=2.0 Hz & J=8.2 Hz, H4)
9.26 ppm (s; 1H; φ—OH)
Description of the Carbon 13 Spectrum of 3
54.2 ppm; (1 CH3; OCH3)
54.3 ppm; (1 CH3; OCH3)
67.4 ppm; (1 CH; CH—OH)
106.4 ppm; (1 CH; CH—(OCH3)$_2$)
115.1 ppm; (1 CHφ; C1)
118.7 ppm; (1 Cq; CHφ; C3)
127.8 ppm; (1 CH & 1Cq; Cqφ—CH and CHφ in C2)
128.4 ppm; (1 CH; CHφ in C4)
154.6 ppm; (Cq; Cqφ—OH)

EXAMPLE 2

Starting from:

1 mole of phenol 5 moles of 60% aqueous dimethoxyethanal 1 mole of soda 30% diluted in water and heating the reaction medium for 5 hours to 60° C., then cooling it to ambient temperature, a crude solution is obtained containing 58.5% of 4-(1-hydroxy-2,2-dimethoxy-ethyl)-phenol 2 and 5% of 2-(1-hydroxy-2,2-dimethoxy-ethyl)-phenol 3, i.e. in total a yield of 63.5% relative to the phenol introduced.

EXAMPLE 3

Starting from:

5 moles of phenol 1 mole of 60% aqueous dimethoxyethanal 1 mole of 100% soda in tablet form and heating the reaction medium for 2 hours in reflux, a crude solution is obtained containing 35% of 4-(1-hydroxy-2,2-dimethoxy-ethyl)-phenol 2 and 44% of 2-(1-hydroxy-2,2-dimethoxy-ethyl)-phenol 3, i.e. in total a yield of 79% relative to the dimethoxyethanal introduced.

EXAMPLE 4

Starting from:

1 mole of phenol 5 moles of 60% aqueous dimethoxyethanal 1 mole of 100% soda in tablet form and heating the reaction medium for 3 hours in reflux, a crude solution is obtained containing 54% of 4-(1-hydroxy-2,2-dimethoxy-ethyl)-phenol 2 relative to the phenol introduced.

EXAMPLE 5

There are introduced into a 500 ml flask:

262.4 g (2 moles) of parachlorophenol 34.7 g (0.2 mole) of dimethoxyethanal in 60% aqueous solution 37.4 g (0.2 mole) of tributylamine.

The reaction mixture is raised to 60° C. and left to react for 14 hours at 60° C. The mixture is cooled to ambient temperature and 404 g of 20% aqueous soda is added and then 100 ml of water.

The aqueous phase is extracted with 200 ml of MTBE, then a second time, with 100 ml of MTBE. The aqueous phase is then neutralized at pH 5 by a 20% HCI solution then it is extracted with 200 ml then 100 ml of MTBE. The organic phase obtained is then concentrated under reduced pressure and 318 g of a crude reaction mixture is obtained.

The excess chlorophenol is then distilled under reduced pressure from this crude reaction mixture. A new crude reaction mixture is then obtained containing 26% of the 4-chloro-2-(1-hydroxy-2,2(dimethoxy-ethyl)-phenol 4 relative to the dimethoxy-ethanal used and residual chlorophenol. The compound 4 was able to be purified by recrystallization from toluene (crystallization yield: 61%) and it gives a white solid having the following characteristics:

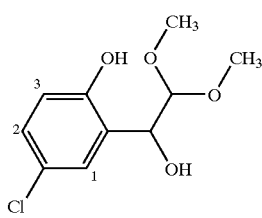

4

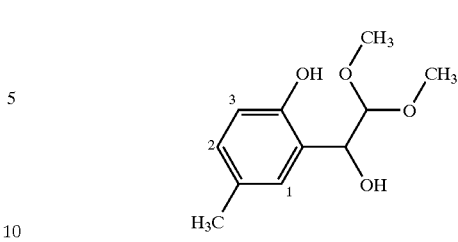

5

Melting point: 58° C.

Description of the Proton Spectrum of 4

3.21 ppm (s; 3H; OCH3)
3.30 ppm (s; 3H; OCH3)
4.37 ppm (d; J=5.1 Hz; 1 H; CH—(OCH3)$_2$)
4.86 ppm (dd; J=5.5 Hz & J=5.1 Hz; 1H; CH—OH)
5.30 ppm (d; J=5.1 Hz; 1 H; CH—OH)
6.77 ppm (d; J=8.6 Hz; 1H; H3)
7.08 ppm (dd; J=8.6 Hz & J=2.7 Hz; 1H; H2)
7.26 ppm (d; J=2.7 Hz; 1H; H1)
9.62 ppm (s; 1 H; φ—OH)

Description of the Carbon 13 Spectrum of 4

54.4 ppm; (1 CH3; OCH3)
54.5 ppm; (1 CH3; OCH3)
66.7 ppm; (1 CH; CH—OH)
106.1 ppm; (1 CH; CH—(OCH3)$_2$)
116.6 ppm; (1 CH; CHφ in 3)
122.3 ppm; (1 Cq; Cqφ—Cl)
127.4 ppm; (1 CH; CHφ; C2)
128.0 ppm; (1 CH; CHφ; C1)
130.2 ppm; (1 Cq; Cqφ—CH)
153.5 ppm; (Cq; Cqφ—OH)

EXAMPLE 6

There are introduced into a 250 ml flask:

108 g (1 mole) of paracresol
34.7 g (0.2 mole) of dimethoxyethanal in 60% aqueous solution
37.4 g (0.2 mole) of tributylamine.

The reaction mixture is raised to 60° C. and left to react for 25 hours at 60° C. The mixture is cooled to ambient temperature and 198.5 g of 20% aqueous soda is added. The supernatant organic phase containing most of the tributylamine is eliminated. The resultant aqueous phase is then extracted with 2 times 100 ml of MTBE. The aqueous phase is then neutralized at pH 5 with a 20% aqueous HCl solution, then extracted with 100 ml of MTBE.

After concentration under reduced pressure of the organic phase, 117.5 g of a crude reaction mixture is obtained, containing 2-(1-hydroxy-2,2-dimethoxy-ethyl)-4-methyl-phenol 5 with a yield of 36% relative to the dimethoxyethanal introduced and paracresol in excess.

After distillation under reduced pressure of the excess paracresol, the expected compound 5 is obtained with a yield of 29% relative to the dimethoxyethanal introduced.

Its spectral characteristics are as follows:

Description of the Proton Spectrum of 5

2.19 ppm (s; 3H; φ—CH3)
3.18 ppm (s; 3H; OCH3)
3.32 ppm (s; 3H; OCH3)
4.39 ppm (d; J=5.5 Hz; 1H; CH—(OCH3)$_2$)
4.33 ppm (d; J=5.9 Hz; 1H; CH—OH)
5.12 ppm (s broad; 1 H; CH—OH)
6.66 ppm (d; J=8.2 Hz; 1H; H3)
6.85 ppm (dd; J=7.8 Hz & J=1.6 Hz; 1H; H2)
7.06 ppm (d; J=1.6 Hz; 1H; H1)
9.03 ppm (s; 1H; φ—OH)

Description of the Carbon 13 Spectrum of 5

20.3 ppm; (1 CH3; φCH3)
54.1 ppm; (2 CH3; OCH3)
67.5 ppm; (1 CH; CH—OH)
b 106.3ppm; (1 CH; CH—(OCH3)$_2$)
114.9 ppm; (1 CH; CHφ in C3)
126.8 ppm; (1 Cq; Cqφ)
127.4 ppm; (1 Cq; Cqφ)
128.1 ppm; (1 CH; CHφ; C2)
128.7 ppm; (1 CH; CHφ; C1)
152.3 ppm; (Cq; Cqφ—OH)

EXAMPLE 7

There are introduced into a flask:

150 g (1 mole) of paratert-butylphenol
34.7 g (0.2 mole) of dimethoxyethanal in 60% aqueous solution
37.4 g (0.2 mole) of tributylamine.

The reaction mixture is raised to 60° C. and left to react for 28 hours at 60° C.

A crude reaction mixture is obtained containing 41%, relative to the dimethoxyethanal introduced, of 4-tert-butyl-2-(1-hydroxy-2,2-dimethoxy-ethyl)-phenol 6. This crude reaction mixture is cooled to ambient temperature and 1600 g of water is added then 170 g of 20% aqueous soda. The aqueous phase is extracted 3 times with 200 ml of MTBE, then it is neutralized at pH 5 by a 20% aqueous HCl solution.

The aqueous phase is then extracted with 500 ml of MTBE, the organic phase resulting from this being concentrated under reduced pressure. 91.7 g of a crude reaction mixture is then obtained, containing paratert-butylphenol in excess and the expected product 6.

After distillation under reduced pressure of the excess paratert-butylphenol, the expected product 6 is obtained with a yield of 34% relative to the dimethoxyethanal introduced. After recrystallization from cyclohexane, the expected product 6 is obtained with a yield of 28% relative to the dimethoxyethanal introduced.

Its characteristics are as follows:
Melting point: 86° C.
Description of the Proton Spectrum of 6
1.23 ppm (s; 9H; φ-(CH3)3)
3.17 ppm (s; 3H; OCH3)
3.30 ppm (s; 3H; OCH3)
4.39 ppm (d; J=5.9 Hz; 1H; CH—(OCH3)2)
4.83 ppm (dd; J=5.5 Hz & J=5.5 Hz; 1H; CH—OH)
5.15 ppm (d; 1H; J=5.1 Hz; CH—OH)
6.66 ppm (d; J=8.6 Hz; 1H; H3)
7.07 ppm (dd; J=7.8 Hz & J=2.7 Hz; 1 H; H2)
7.28 ppm (d; J=2.2 Hz; 1H; H1)
9.04 ppm (s; 1H; φ—OH)
Description of the Carbon 13 Spectrum of 6
31.4 ppm; (3 CH3; φ-(CH3)3)
33.7 ppm; (1 Cq; Cq Tbu)
54.2 ppm; (2 CH3; OCH3)
67.8 ppm; (1 CH; CH—OH)
106.3 ppm; (1 CH; CH—(OCH3)2)
114.5 ppm; (1 CH; CHφ; C3)
124.3 ppm; (1 CH; CHφ; C2)
125.0 ppm; (1 CH; CHφ; C1)
126.7 ppm; (1 Cq; Cqφ—CH)
140.5 ppm; (1 Cq; Cqφ)
152.2 ppm; (Cq; Cqφ—OH)

EXAMPLE 8

There are introduced into a flask:

17.3 g (0.1 mole) of dimethoxyethanal in 60% aqueous solution
125.4 g (1 mole) of guaiacol
18.7 g (0.1 mole) of tributylamine The mixture is heated to 60° C. and left to react with constant stirring at this temperature for 24 hours.

After cooling, 161 g of a crude reaction mixture is obtained, containing in particular the excess guaiacol, the tributylamine and the condensation products present in the form of 2 isomers, probably ortho and para, of the hydroxyl group of the phenol in the proportions 72/28.

65 g of this crude mixture is concentrated under reduced pressure in order to eliminate most of the water then the excess guaiacol and the tributylamine, to give 7.6 g of a brown oily residue enriched in expected compounds which can then be analysed by CPG/mass spectrometry coupling which gives the following spectra:

1st (majority) isomer 7a: MS/IE: 228 (M+)
Principal fragments: 210, 196, 167, 165, 153, 151, 137, 133, 125, 109, 93, 81, 75, 65, 53, 47
2nd (minority) isomer 7b: MS/IE: 228 (M+) Principal fragments: 210, 196, 167, 165, 153, 151, 137, 133, 125, 109, 93, 81, 75, 65, 53, 47

EXAMPLE 9

There are introduced into a flask:
35.1 g (0.2 mole) of dimethoxyethanal in 60% aqueous solution
153.7 g (1 mole) of methyl parahydroxybenzoate
37.4 g (0.2 mole) of tributylamine The mixture is left to react with constant stirring at 60° C. for 23 hours then a further 27 hours at 70–75° C.

The mixture is cooled to ambient temperature, the excess methyl parahydroxybenzoate precipitates.

After filtration, 92 g of a brown-coloured filtrate is obtained, enriched in 3-(1-hydroxy-2,2-dimethoxy-ethyl)-4-hydroxy-methylbenzoate 8, the spectral characteristics of which are as follows:

Description of the Proton Spectrum
3.19 ppm (s; 3H; O—CH3)
3.30 ppm (s; 3H; O—CH3)
3.78 ppm (s; 3H; COOCH3)
4.37 ppm (d; J=5.1 Hz; 1H; CH—(OCH3)2)
4.9 ppm (d; J=5.5 Hz; 1H; CH—OH)
6.84 ppm (d; J=8.6 Hz; 1H; H5)
7.69 ppm (dd; J=8.4 Hz & J=2.2 Hz; 1H; H6)
7.94 ppm (d; J=2Hz; 1H; H2)
Description of the Carbon 13 Spectrum
51.6 ppm; (1 CH3; COOCH3)
54.4 ppm;(1 CH3; OCH3)
54.5 ppm; (1 CH3; OCH3)
66.7 ppm; (1 CH; CH—OH)
106.4 ppm; (1 CH; CH—(OCH3)2)
115.0 ppm; (1CH; CHφ; C5)
120.3 ppm; (1 Cq; Cqφ—COOMe; C1)
128.3 ppm; (1 Cq; Cqφ—Ch; C3)
129.6 ppm; (1 CH; CHφ; C2 or C6)
130.3 ppm; (1 CH; CHφ; C6 or C2)
159.2 ppm; (1 Cq; Cqφ—OH; C4)
166.1 ppm; (1 Cq; COOMe)

EXAMPLE 10

The aim of the examples is to show the thermocrosslinking properties of the phenolic compounds derived from dialkoxyethanals of formula (I) and their salts with the alkali metals, alkaline-earth metals and amines.

a) Preparation of the Samples

Sample 1

5 g of the crystallized compound described in example 1 is solubilized in 5 g of distilled water. Whatman no. 1 paper is then impregnated with the obtained solution (pH about 5).

Once impregnated, the paper is allowed to drip, dried for 12 hours at ambient temperature then at 40° C. for an hour.

Sample 2

4.4 g of the crystallized compound described in example 1 and 0.3 g of hexahydrated magnesium chloride are solubilized in 4.4 g of distilled water.

Whatman no. 1 paper is then impregnated with the obtained solution. Once impregnated, the paper is allowed to drip, dried for 12 hours at ambient temperature then at 40° C. for an hour.

Sample 3

Whatman no. 1 paper is impregnated with the crude solution obtained in example 4.

Once impregnated, the paper is allowed to drip, dried for 12 hours at ambient temperature then at 40° C. for an hour.

Sample 4

4.2 g of magnesium chloride hexahydrate is solubilized in 100 g of crude solution of Example 4.

Whatman no. 1 paper is then impregnated with the obtained solution. Once impregnated, the paper is allowed to drip, dried for 12 hours at ambient temperature then at 40° C. for an hour.

b) ATMD Measurement of the Prepared Samples

The different paper samples are then tested in ATMD in the following conditions:

apparatus: ATMD MKIII (Rheometrics)—sensor: mixed up to 500° C.

Mode: "Double beam mode" (Dual Bending Cantilever)

Frequency: 1 Hz

Heating rate, temperature: 4.0° C./mn, from 30° C. to 240° C.

Dimensions of the sample: 2×10×0.2 mm

The crosslinking is made visible by the variation of the E' modulus (elastic modulus) in relation to the temperature: cf. attached graphs.

In all cases, it is noted that a crosslinking takes place through an increase and a change in pitch of log (E') at temperatures above 110° C.

For samples 1 and 2, respectively without or with catalyst, crosslinking starts around 135° C.–140° C.; for samples 3 and 4, respectively without or with catalyst, the start of crosslinking operates around 165° C. and 175° C.

It will be noted that the Whatman no. 1 paper alone experiences no variation in modulus of the same type in the same conditions.

What is claim is:

1. New phenolic compounds derived from dialkoxyethanals of formula (I)

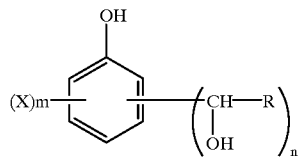

in which

R is a dialkoxymethyl group with from 3 to 17 carbon atoms, a 1,3-dioxolan-2-yl group optionally substituted on peaks 4 and/or 5 by one or more alkyl groups comprising from 1 to 8 carbon atoms or a 1,3-dioxan-2-yl group optionally substituted on peaks 4.0 and/or 5 and/or 6 by one or more alkyl groups comprising from 1 to 8 carbon atoms, n has the value 1, 2 or 3 and the group or groups

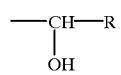

are in ortho and/or in para position of the OH group of the cycle m represents from 0 to 4-n and X represents a functional group selected from the group of: hydroxyl; halogen; an alkyl or alkoxy group comprising from 1 to 8 carbon atoms; aryl group comprising from 5 to 12 carbon atoms and optionally 1 or 2 heteroatoms such as nitrogen or oxygen; carboxy; a —CO—Y group in which Y represents an alkyl or alkoxy radical containing from 1 to 8 carbon atoms; amido radical; amino radical or thiol radical with the exception of the compound 1

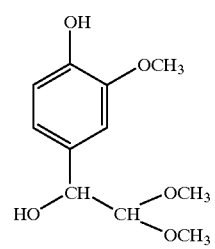

or their salt with the alkali metal, alkaline-earth metal and amine.

2. Preparation process for phenolic compounds of formula (I) according to claim 1, or their salt with the alkali metal, alkaline-earth metal and amine comprising the steps of:

reacting a phenol of formula (II)

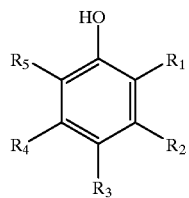

(II)

in which $R_1$, $R_2$, $R_3$, $R_4$, $R_5$ are independantly selected from the group consisting of: hydroxyl radical; halogen; hydrogen; an alkyl or alkoxy group comprising from 1 to 8 carbon atoms; aryl group comprising from 5 to 12 carbon atoms and optionally 1 or 2 heteroatoms such as nitrogen or oxygen; carboxy; a —CO—Y group in which Y represents an alkyl or alkoxy radical containing from 1 to 8 carbon atoms; amido radical; amino radical or thiol radical, on condition that at least one of the ortho or pare positions of the phenolic cycle is substituted by a hydrogen;

with an aldehyde of formula (III)

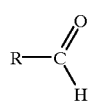

(III)

in which R is a dialkoxymethyl group with from 3 to 17 carbon atoms, a 1,3-dioxolan-2-yl group optionally substituted on peaks 4 and/or 5 by one or more alkyl groups comprising from 1 to 8 carbon atoms or a 1,3-dioxan-2-yl group optionally substituted on peaks 4 and/or 5 and/or 6 by one or more alkyl groups comprising from 1 to 8 carbon atom in the presence of a base.

3. Process according to claim 2, where 1 mole of phenol of formula (II) is reacted with 0.1 to 10 moles of aldehyde of formula (III) in the presence of 0.1 to 2 moles of base.

4. Process according to claim 3, where 1 mole of phenol of formula (II) is reacted with 0.1 to 5 moles of aldehyde of formula (III) in the presence of 0.1 to 1 mole of base.

5. Process according to claim 2 where said base is a tertiary amine.

6. Process according to claim 5, where said base is tributylamlne or triethylamine.

7. Process according to claim 2, where said base is a hydroxide of alkali metal.

8. Process according to claim 7, where said base is sodium hydroxide or potassium hydroxide.

9. Process according to claim 2, where said base is a carbonate of alkali metal.

10. Process according to claim 9, where said base is sodium carbonate or potassium carbonate.

11. Process according to claim 2, where the product of formula (III) is dimethoxyacetaldehyde, diethoxyacetaldehyde, dibutoxyacetaldehyde, 2-formyl-1,3-dioxolane or 5,5-dimethyl 2-formyl 1,3-dioxane.

12. A process for the crosslinking without formaldehyde of a substrate comprising the steps of:

providing a substrate;

providing phenolic compounds of formula (I) or their salt with the alkali metal, alkaline-earth metal and amine, according to claim 1; and crosslinking said substrate with said phenolic compounds.

13. The process of claim 12 wherein the substrate is selected from the group consisting of a cellulose substrate, a nylon substrate, a polyester substrate, and a glass substrate.

14. The new phenolic compounds according to claim 1 where said halogen is selected from: chlorine, fluorine, bromine or iodine.

15. The process of claim 12 wherein the substrate is a non-woven substrate.

* * * * *